(12) United States Patent
Falb et al.

(10) Patent No.: US 8,759,382 B2
(45) Date of Patent: Jun. 24, 2014

(54) PROPARGYL-TRIFLUOROMETHOXY-AMINOBENZOTHIAZOLE DERIVATIVES, THEIR PREPARATION AND USE

(75) Inventors: Eliezer Falb, Givatayim (IL); Jeffrey Sterling, Tel Mond (IL); Yaacov Herzig, Raanana (IL); Raphael Nudelman, Rehovot (IL); Konstantin Ulanenko, Netanya (IL)

(73) Assignee: Teva Pharmaceutical Industries Ltd., Petach-Tikva (IL)

( * ) Notice: Subject to any disclaimer, the term of this patent is extended or adjusted under 35 U.S.C. 154(b) by 0 days.

(21) Appl. No.: 13/823,001

(22) PCT Filed: Sep. 29, 2011

(86) PCT No.: PCT/US2011/053979
§ 371 (c)(1),
(2), (4) Date: Mar. 13, 2013

(87) PCT Pub. No.: WO2012/050971
PCT Pub. Date: Apr. 19, 2012

(65) Prior Publication Data
US 2013/0172364 A1    Jul. 4, 2013

Related U.S. Application Data

(60) Provisional application No. 61/387,664, filed on Sep. 29, 2010, provisional application No. 61/393,783, filed on Oct. 15, 2010.

(51) Int. Cl.
*A01N 43/78* (2006.01)
*A61K 31/425* (2006.01)
*C07D 277/60* (2006.01)
*C07D 277/62* (2006.01)

(52) U.S. Cl.
USPC .......................................... 514/367; 548/152

(58) Field of Classification Search
CPC ... C07D 277/62; C07D 277/64; C07D 277/82
USPC .......................................... 514/367; 548/152
See application file for complete search history.

(56) References Cited

U.S. PATENT DOCUMENTS

| | | | |
|---|---|---|---|
| 5,169,868 | A | 12/1992 | Yu et al. |
| 6,849,632 | B2 | 2/2005 | Zablocki et al. |
| 2004/0162282 | A1 | 8/2004 | Pennell et al. |
| 2006/0235024 | A1 | 10/2006 | Bryan et al. |

FOREIGN PATENT DOCUMENTS

| | | |
|---|---|---|
| WO | WO 93/21169 A1 | 10/1993 |
| WO | WO 2004/047756 A2 | 6/2004 |
| WO | WO 2010/086860 A2 | 8/2010 |

OTHER PUBLICATIONS

Notification of Transmittal of the International Search Report and the Written Opinion of the International Searching Authority, or the Declaration, including an International Search Report and Written Opinion of the International Searching Authority, mailed Apr. 20, 2012 in connection with PCT International Application No. PCT/US2011/053979, filed Sep. 29, 2011.

*Primary Examiner* — Kendra D Carter
(74) *Attorney, Agent, or Firm* — John P. White; Cooper & Dunham LLP (57) ABSTRACT

Disclosed are novel derivatives of propargyl-trifluoromethoxy-amino-benzothiazole which are effective in treating neurologic disorders, including Parkinson's disease and multiple sclerosis.

17 Claims, 2 Drawing Sheets

PROPARGYL-TRIFLUOROMETHOXY-AMINOBENZOTHIAZOLE DERIVATIVES, THEIR PREPARATION AND USE

CROSS-REFERENCE TO RELATED APPLICATIONS

This application is a §371 national stage of PCT International Application No. PCT/US2011/053979, filed Sep. 29, 2011, claiming the benefit of U.S. Provisional Applications Nos. 61/393,783, filed Oct. 15, 2010 and 61/387,664, filed Sep. 29, 2010, the contents of each of which are hereby incorporated by reference in its entirety.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Neurologic disorders are becoming increasingly common. Thus, developing an effective treatment for neurologic disorders has become a high priority in the drug industry.

Neurologic disorders can generally be divided into two groups based on their physiological and pathological characteristics. Parkinson's disease, Alzheimer's disease, Huntington's disease and amyotrophic lateral sclerosis (ALS or Lou Gehrig's disease) are all progressive disorders (i.e., their symptoms are not apparent until months or more commonly years after the disease has begun), caused by an initial reduction of neuronal function, followed by a complete loss of function upon neuronal death. In addition, these progressive neurologic disorders are characterized by the presence of protein aggregates that are believed to hamper cellular functions (e.g., neurotransmission), and may ultimately result in cell death (Sasaki et al., Am. J. Pathol., 153:1149-1155 [1998]).

Multiple sclerosis is a disorder of the central nervous system, which is slowly progressive and is characterized by disseminated patches of demyelination in the brain and spinal cord, resulting in multiple and varied neurologic symptoms and signs, usually with remissions and exacerbations. The cause is unknown but an immunologic abnormality is suspected (THE MERCK MANUAL, 18th EDITION, 2009 MERCK & CO.). Several different drug therapies are currently being investigated.

While the aforementioned disorders are all slowly progressive, neurological dysfunction can also be caused by a more abrupt event such as an infarction of brain tissue, or stroke. Brain stroke is the third leading cause of death in the developed countries. Survivors often suffer from neurological and motor disabilities. The majority of central nervous system ("CNS") strokes are regarded as localized tissue anemia following obstruction of arterial blood flow which causes oxygen and glucose deprivation. R(+)-N-propargyl-1-aminoindan has been shown to be an effective treatment for stroke and traumatic brain injury (See, e.g. U.S. Pat. No. 5,744,500).

A series of propargylamines, including Selegiline and Rasagiline, have been shown to prevent apoptosis in dopamine neurons in Parkinson's models (Naoi, M. et al. J. Neural Transmission (2002) 109: 607-721). N-Propargyl-1-Aminoindan has been shown to be useful for treating Parkinson's disease, dementia and depression (See, e.g. U.S. Pat. No. 5,453,446). The mechanism by which the propargylamines confer neuroprotection is not fully understood. However, it is clear that the mechanism involves a complex set of neurochemical events including alterations in Bcl-2, GAPDH, SOD and catalase (Youdim, M. B. H. Cell. Mol. Neurobiol. (2001) 21(6): 555-573).

However, additional agents to treat neurodegenerative diseases are needed.

SUMMARY OF THE INVENTION

The subject invention provides novel derivatives of propargyl-trifluoromethoxy-amino-benzothiazole which are effective at treating neurologic disorders, including Parkinson's disease, and multiple sclerosis.

The subject invention provides a compound according to the formula:

wherein $R_1$ is $-CH_2NR_2-$ or an N-containing heterocycloalkyl, wherein $R_2$ is H or C1-C4 alkyl, or a pharmaceutically acceptable salt thereof.

The subject invention also provides a pharmaceutical composition comprising the compound described herein or a pharmaceutically acceptable salt thereof, and a pharmaceutically acceptable carrier.

The subject invention further provides a process of preparing a compound having the structure:

comprising the steps of:
a) reacting under suitable conditions with an halide acid (e.g. HBr) in the presence of a first solvent;
b) adding piperazine to the reaction mixture of step a) to provide c) reacting the product from step b) with propargylhalide (e.g. propargylbromide) in the presence of a second solvent; and
d) obtaining the compound from the reaction mixture of step c).

The subject invention yet further provides a process of manufacturing a compound having the structure:

wherein R is H or C1-C4 alkyl,
comprising the steps of:
a) reacting under suitable conditions with Lawesson's Reagent in the presence of a first solvent to provide b) reacting the product from step a) with an oxidizing agent (e.g. K₂Fe(CN)₆) in the presence of a second solvent to provide c) reacting the product from step b) with N-bromosuccinimide in the presence of a third solvent to provide and
d) reacting the product from step c) with in the presence of a fourth solvent; and
e) obtaining the compound from the reaction mixture of step d).

The subject invention yet further provides a method for treating a subject afflicted with an autoimmune disorder comprising administering to the subject a therapeutically effective amount of the compound described herein or a pharmaceutically acceptable salt thereof, or the pharmaceutical composition described herein, so as to thereby treat the autoimmune disorder in the subject.

DETAILED DESCRIPTION OF THE INVENTION

The subject invention provides a compound according to the formula:

wherein $R_1$ is —$CH_2NR_2$— or an N-containing heterocycloalkyl, wherein $R_2$ is H or C1-C4 alkyl, or a pharmaceutically acceptable salt thereof.

In the above formula, when $R_1$ is —$CH_2NR_2$—, $R_1$ is connected to the benzothiazole ring via the —$CH_2$ group.

In an embodiment of the compound, $R_1$ is N-containing heterocyclohexane, or a pharmaceutically acceptable salt of the compound.

In another embodiment of the compound, the N-containing heterocyclohexane is piperazine or piperidine, or a pharmaceutically acceptable salt thereof.

In yet another embodiment of the compound, $R_1$ is piperazine, or a pharmaceutically acceptable salt of the compound.

In yet another embodiment of the compound, the compound has the formula:

or a pharmaceutically acceptable salt thereof.

In yet another embodiment of the compound, $R_1$ is —$CH_2NR_2$—, and $R_2$ is selected from the group consisting of H and $CH_3$, or a pharmaceutically acceptable salt of the compound.

In yet another embodiment of the compound, the compound has the formula:

or a pharmaceutically acceptable salt thereof.

In yet another embodiment of the compound, the compound has the formula:

or a pharmaceutically acceptable salt thereof.

In yet another embodiment of the compound, the compound is in the form of a hydrochloride salt.

In yet another embodiment of the compound, the compound is in the form of a mesylate salt.

The subject invention also provides a pharmaceutical composition comprising the compound described herein or a pharmaceutically acceptable salt thereof, or the salt described herein, and a pharmaceutically acceptable carrier.

The subject invention further provides a process of preparing a compound having the structure:

comprising the steps of:
a) reacting under suitable conditions with an halide acid (e.g. HBr) in the presence of a first solvent;
b) adding piperazine to the reaction mixture of step a) to provide c) reacting the product from step b) with propargylhalide (e.g. propargylbromide) in the presence of a second solvent; and
d) obtaining the compound from the reaction mixture of step c).

In an embodiment of the process, the first solvent is a mixture of toluene and acetic acid, and the second solvent is toluene.

The subject invention yet further provides a process of manufacturing a compound having the structure:

wherein R is H or C1-C4 alkyl,
comprising the steps of:
a) reacting under suitable conditions with Lawesson's Reagent in the presence of a first solvent to provide b) reacting the product from step a) with an oxidizing agent (e.g. K$_2$Fe(CN)$_6$) in the presence of a second solvent to provide c) reacting the product from step b) with N-bromosuccinimide in the presence of a third solvent to provide and
d) reacting the product from step c) with in the presence of a fourth solvent; and
e) obtaining the compound from the reaction mixture of step d).

In an embodiment of the process, the first solvent is THF, the second solvent is ethanol, the third solvent is CCl$_4$, and the fourth solvent is acetonitrile.

The subject invention yet further provides a method for treating a subject afflicted with an autoimmune disorder comprising administering to the subject a therapeutically effective amount of the compound described herein or a pharmaceutically acceptable salt thereof, or the pharmaceutical composition described herein, so as to thereby treat the autoimmune disorder in the subject.

In an embodiment of the method, the autoimmune disorder is multiple sclerosis.

In an embodiment of the method, the therapeutically effective amount is from about 1 to about 1000 mg/day.

In an embodiment of the method, the therapeutically effective amount is from about 0.1 to about 10 mg/kg/day.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

A "pharmaceutically acceptable salt" of the compounds of the invention includes those formed with both organic and inorganic acids or bases. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p 1445, the disclosure of which is hereby incorporated by reference.

The subject invention is intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography, elemental analysis, Ames test, dissolution, stability and any other quality that can be determined by an analytical method. Once the characteristics of a compound are known, the information can be used to, for example, screen or test for the presence of the compound in a sample.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n−1 or n carbons in a linear or branched arrangement, and specifically includes methyl, ethyl, propyl, butyl, pentyl, hexyl, and so on.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, an "isolated" compound refers to a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to eliminate the presence of chemical entity in the composition.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R §211.166, the entire content of which is hereby incorporated by reference.

As used herein, a "neurodegenerative disorder" includes Parkinson's disease, Restless Legs Syndrome, Multiple System Atrophy (MSA), Progressive Supranuclear Palsy (PSP), Glaucoma, Macular Degeneration, Hearing loss, and Retinitis Pigmentosa.

As used herein, "about" in the context of a numerical value or range means±10% of the numerical value or range recited or claimed.

Specific examples of pharmaceutically acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

By any range disclosed herein, it is meant that all hundredth, tenth and integer unit amounts within the range are specifically disclosed as part of the invention. Thus, for example, 0.01 mg to 50 mg means that 0.02, 0.03 ... 0.09; 0.1, 0.2 ... 0.9; and 1, 2 ... 49 mg unit amounts are included as embodiments of this invention. For example, a range of 0.01-20 mg means that all hundredth, tenth and integer unit amounts within the range are specifically disclosed as part of the invention. Thus, 0.02, 0.03 ... 0.09; 0.1, 0.2 ... 0.9; and 1, 2 ... 19 mg unit amounts are included as embodiments of this invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Synthesis of Compound A 2-(piperazin-1-yl)-6-(trifluoromethoxy)benzo[d]thiazole 6-trifluoromethoxybenzothiazole-2-amine (riluzole, 5 g, 0.0213 mol) was dissolved in a mixture of toluene/AcOH (26 ml and 12 ml, respectively) and aqueous HBr (48%, 16.5 ml) was then added to give a white suspension. Into this suspension, a water solution of NaNO$_2$ (Sodium Nitrite, 5.6 g in 7.9 ml) cooled to 0° C. (ice water bath) was added dropwise (within ~10-15 min). During addition, gas evolved after which the mixture was stirred for ¼ h. at 0-5° C. TLC (hexane:EtOAc—2:1) indicated complete consumption of riluzole and clean formation of the product 6-trifluoromethoxybenzothiazole-2-bromo. Then the reaction mixture was diluted with water (50 ml) and toluene (50 ml). The organic phase was separated from the water phase which was extracted with toluene (2×50 ml). The combined toluene phase was washed with 10% Na$_2$CO$_3$ (until pH=5-6) and concentrated to volume of 40 ml into which piperazine (3.7 g, 2 eq, 0.426 mole) was added. The reaction mixture was stirred at rt overnight after which time TLC (hexane:EtOAc—1:1) still showed starting material and also a new product slightly beneath (in TLC) the starting material and also a strong spot at the start of the TLC plate. This spot could be "moved" by a mixture of DCM:MeOH—90:10 as the mobile phase in TLC. The spot which had UV absorption could be stained by ninhydrin spray and heating of the TLC plate. Hence, reaction mixture was filtered and filtrate evaporated to give ~6 g of yellow solid. Half of the latter solid was purified (on a Combiflash® personal flash chromatography instrument, 3.3 g crude yellow solid were impregnated on silica gel and loaded on the machine) to give 2.85 (44%) of 2-(piperazin-1-yl)-6-(trifluoromethoxy)benzo[d]thiazole as a yellow solid.

2-(4-(prop-2-ynyl)piperazin-1-yl)-6-(trifluoromethoxy)benzo[d]thiazole (Compound A)

2-(piperazin-1-yl)-6-(trifluoromethoxy)benzo[d]thiazole (1 g, 3.29 mmol) was dissolved in $CH_3CN$ (20 ml) and $K_2CO_3$ (0.46 g, 3.3 mmol) and propargylbromide (0.6 g, 80% in toluene, 4 mmol, 1.22 eq) were added and the heterogeneous reaction mixture was stirred at room temperature and progress of the reaction was monitored by TLC (DCM:MeOH—90:10 ($R_{fSM}$=18%) and EtOAC:hexane—1:1 or 1:2 ($R_{fproduct}$=65%)). After ~5 h most of the starting material was consumed but since some starting material was still present additional amount of $K_2CO_3$ and propargylbromide were added (0.2 g and 150 μl, respectively) and the reaction was continued overnight, after which time TLC indicated almost complete reaction. The reaction mixture was filtered and filtrate evaporated to leave a wet solid which was then dissolved in DCM and evaporated and this process was repeated once more to leave a dry solid (~1.3 g) which was impregnated on silica gel (0.06-0.02 Merck) and loaded on a Combi-flash® personal flash chromatography instrument and purification was performed to give a yellowish solid. About 500 mg of this solid were dissolved in $Et_2O$ and then HCl/IPA was added (few drops) to give a white solid which was precipitated from the mother liquor. The solid was filtered, washed well with $Et_2O$ and vacuum dried to give ~550 mg of the HCl salt of the title compound. $^1$H-NMR of the HCl salt ($DMSOd_6$) δ 8.01 (s, 1H, Ar), 7.58 (d, 1H, Ar), 7.32 (d, 1H, Ar), 4.16 (s, 2H, $CH_2$), 3.89 (s, 1H, CH) 3.12-3.8 (two br s, 8H, piperazine); $^{13}$C-NMR of the HCl salt ($DMSOd_6$) δ 169.20, 151.32, 143.23, 132.22, 120.69, 120.31, 119.99, 115.53, 82.00, 73.49, 49.64, 45.20, 44.72; LCMS (ES-API for free base) 341.08.

Example 2

Synthesis of Compound B and Compound C

N-(4-(trifluoromethoxy)phenyl)ethanethioamide

N-(4-(trifluoromethoxy)phenyl)acetamide (112 g, 0.511 mol) was dissolved in THF (400 ml) and Lawesson's Reagent (2,4-bis(4-methoxyphenyl)-1,3,2,4-dithiadiphosphetane 2,4-disulfide) (100 g, 0.247 mol) was added. The suspension was stirred at rt for 3 days, then filtered, filtrate evaporated and the residue was purified by chromatography (20% EtOAc in hexane) to give 100.5 g (84%) of N-(4-(trifluoromethoxy)phenyl)ethanethioamide.

2-methyl-6-(trifluoromethoxy)benzo[d]thiazole

N-(4-(trifluoromethoxy)phenyl)ethanethioamide (38 g, 0.162 mol) was dissolved in EtOH (70 ml), water solution of NaOH (52.5 g, in 175 ml water) was added and the solution was diluted with 350 ml water. This solution was then added drop wise, within 30 min., into a solution of $K_2Fe(CN)_6$ (210 g) in 520 ml water at 85-95° C. The reaction mixture was then stirred at 85-95° C. for 1 hr and cooled. TLC (7:3-hexane:EtOAc) was performed. The product was extracted with DCM, the organic phase was dried over $Na_2SO_4$, filtered and evaporated and the residue was purified by flash column chromatography (5% EtOAc in hexane) to give 16.8 g (44.5%) of 2-methyl-6-(trifluoromethoxy)benzo[d]thiazole.

2-(bromomethyl)-6-(trifluoromethoxy)benzo[d]thiazole

A mixture of 2-methyl-6-(trifluoromethoxy)benzo[d]thiazole (9 g, 0.0386 mol) and NBS (6.9 g, 0.0386 mol) and benzoyl peroxide (0.25 g) in $CCl_4$ (250 ml) was heated to reflux under lamp light (150 Watt) for 4 hr. Then the mixture was filtered, evaporated and purified using the Combi-Flash instrument to give 4.3 g (28.5%) of di-bromo product, 3.1 g (34%) of starting material and 4.6 g (38.2%) of 2-(bromomethyl)-6-(trifluoromethoxy)benzo[d]thiazole.

N-((6-(trifluoromethoxy)benzo[d]thiazol-2-yl)methyl)prop-2-yn-1-amine (Compound B)

2-(bromomethyl)-6-(trifluoromethoxy)benzo[d]thiazole (3.8 g, 0.0122 mol) and propargylamine (1.7 g, 2.5 eq) were dissolved in acetonitrile (50 ml) and the reaction mixture was heated to reflux for 1 h. Then it was cooled, evaporated to dryness and the residue was partitioned between EtOAc and water, 0.5 ml of $NH_4OH$ was add (pH=9-10) and the organic phase was separated, dried over $Na_2SO_4$, evaporated and the residue purified by chromatography (hexane-EtOAc) to give 3 g (86%) of N-((6-(trifluoromethoxy)benzo[d]thiazol-2-yl)

methyl)prop-2-yn-1-amine. The free base was dissolved in 100 ml Et$_2$O and HCl/IPA was added. The white suspension that was obtained was filtered and dried to give 2.7 g (mp=188-189° C., dec) of white solid, which was identified as the HCl salt of Compound B. $^1$H-NMR (of the HCl salt of the title compound, DMSOd$_6$) δ 10.23 (br s, 2H, NH$_2$), 8.35 (s, 1H, Ar), 8.16 (d, 1H, Ar), 7.57 (d, 1H, Ar), 4.76 (s, 2H, C—CH$_2$) 4.04 (d, 2H, N—CH$_2$—C), 3.74 (s, 1H, CH); $^{13}$C-NMR (DMSOd$_6$) δ 164.40, 150.66, 145.74, 136.53, 124.01, 120.39, 120.10, 115.54, 79.84, 74.88, 46.05, 35.80; LCMS (ES-API for free base) 287.0 (M+H).

N-methyl-N-((6-(trifluoromethoxy)benzo[d]thiazol-2-yl)methyl)prop-2-yn-1-amine (Compound C)

2-(bromomethyl)-6-(trifluoromethoxy)benzo[d]thiazole (4.4 g, 0.0141 mol) and N-Me-propargylamine (2.4 g, 2.5 eq, 0.035 mol) were dissolved in acetonitrile (70 ml) and the reaction mixture was heated to reflux for 1 h. Then it was cooled, evaporated to dryness and the residue was partitioned between EtOAc and water (100 ml:100 ml), NH$_4$OH was add (to give pH of 9-10) and the organic phase was separated, dried over Na$_2$SO$_4$, evaporated and the residue purified by chromatography (hexane-EtOAc) to give 4.1 g (97%) of N-methyl-N-((6-(trifluoromethoxy)benzo[d]thiazol-2-yl)methyl)prop-2-yn-1-amine. The free base (4.1 g) was dissolved in 100 ml Et$_2$O and HCl/IPA (2N) was added (pH=1-2). The white suspension that was obtained was filtered and the collected solid was dried to give 2.7 g (mp=117-120° C.) which was identified to be the HCl salt of compound C. $^1$H-NMR (of the HCl salt of the title compound, DMSOd$_6$) δ 8.38 (s, 1H, Ar), 8.20 (d, 1H, Ar), 7.58 (d, 1H, Ar), 4.86 (br s, 2H, C—CH$_2$) 4.22 (br s, 2H, MeN-CH$_2$—C), 3.88 (s, 1H, CH), 2.89 (s, 3H, NMe); $^{13}$C-NMR (DMSOd$_6$) δ 163.38, 150.96, 145.83, 136.87, 124.36, 120.36, 120.08, 115.46, 81.22, 73.60, 53.50, 44.37; LCMS (ES-API for free base) 301.0 (M+H).

Example 3

Multiple sclerosis (MS) is an immune-mediated disorder of the CNS leading to progressive decline of motor and sensory functions causing permanent disabilities.

EAE induced in the CSJL/FI strain of mice was selected to test the compounds mentioned above, as it is an established EAE model to test the efficacy of candidate molecules for MS treatment.
General Design:

Disease was induced in all mice by the injection of the encephalitogenic emulsion (MSCH/CFA). Treatment was started from day 1 of the study or at disease onset and was administered every day, orally (BID), from onset of the study.
Materials:

Laquinimod, as a positive control, was prepared according to U.S. Application Publication No. 2007/0088050.

Compounds A, B and C were prepared according to Examples 1 and 2 above.

Phosphate bufferred saline (PBS), "Sigma"
Pertusis toxin, "Sigma"
Lyophilized mouse spinal cord homogenate (MSCH)
Complete Freund's Adjuvant (CFA) "Sigma"
Incomplete Freund's adjuvant (ICFA), "Difco"
Experimental Animals:
Species, Strain and Supplier Healthy, nulliparous, non-pregnant female mice of the CSJL/FI strain obtained from Harlan Animal Breeding Center, Jerusalem, Israel were used in the study. The animals weighed about 17-20 g on arrival, and were approximately 9 weeks of age at initiation of the study. Overtly healthy animals were assigned to study groups arbitrarily before treatment commenced.

The mice were individually identified by markings on the body. A color-coded card on each cage provides information including cage number, group number and identification.
Group Assignment:

The mice were allocated to the following 8 groups of 10 mice each:
Experimental Design:

| Treatment Groups | dose /day |
| --- | --- |
| PBS 5% Dextrose (negative control) | 10 ml/kg daily (BD) from Day 0 to 22 |
| Laquinimod (positive control) | 1 mg/kg daily (QD) from Day 0 to 22 |
| Compound B | 25 mg/kg (BID) from Day 0 to 22 |
| | 50 mg/kg (BID) from Day 0 to 22 |
| | 100 mg/kg (BID) from Day 0 to 22 |
| Compound C | 25 mg/kg (BID) from Day 0 to 22 |
| | 50 mg/kg (BID) from Day 0 to 22 |
| | 100 mg/kg (BID) from Day 0 to 22 |

BD or BID: Twice a day
QD: Once a day

Treatments in all groups were administered orally.
Preparation and Administration of Encephalitogenic Emulsion
Oil Portion:
CFA (containing 1 mg/ml *Mycobacterium Tuberculosis* (MT)).
Liquid Portion:
320 mg MSCH was suspended in 4 ml PBS in vial #1 to yield 80 mg/ml MSCH suspension.
Emulsification:

The emulsion was made from equal parts of oil (4 mL CFA containing 1.0 mg/ml MT) and liquid portions (2000 mg MSCH/2.5 mL PBS) in two syringes connected to each other with a Leur lock. The concentration of MSCH in emulsion is 40 mg/mL.

The emulsion was transferred to an insulin syringe before injection. 0.05 ml was injected into the left foot-pad of each mouse.
Preparation and Administration of Pertussis Toxin:

104 μL Pertussis toxin (200 μg/ml) was added to 25.87 ml PBS to yield 800 ng/ml. The pertussis toxin was administered intravenously on the day of the encephalitogen injection and 48 hours later (160.0 ng/0.2 ml/mouse×2=320 ng/mouse).
Preparation and Administration of Working Concentrations of Test Articles:

Laquinimod was diluted in DDW water to yield 0.1 mg/ml. The solution was stored in an amber colored bottle at 2 to 8° C. The 0.1 mg/ml laquinimod was administered orally, once, daily from the initiation of the study until study termination (Day 23).

Compounds B and C were dissolved in 5% Dextrose to concentrations of 2.5, 5.0 and 10 mg/ml for dose levels of 25, 50 and 100 mg/kg respectively. Test samples were freshly prepared. The 2.5, 5.0 and 10 mg/ml concentrations of Compounds B and C were administered orally, twice daily (BID) from initiation of study until study termination (Day 23) to groups Experimental Observations Morbidity and Mortality:

All animals were examined once daily to detect if any is dead or moribund.

Clinical Signs:

Scoring of EAE clinical signs were initiated from the 10th day post-EAE induction and were continued daily. The clinical signs were recorded on observation cards according to a grading system described in the table below.

Evaluation of the EAE Clinical Signs:

| Score | Signs | Description |
|---|---|---|
| 0 | Normal behavior | No neurological signs. |
| 1 | Tail weakness | The mouse tail is limp and droops. |
| 2 | Hind legs weakness | Limb paresis, wobbly walk—when the mouse walks the hind legs are unsteady. |
| 3 | Hind legs paralysis | The mouse can't move its hind legs and it drags them when he walks. |
| 4 | Full paralysis | The mouse can't move its legs at all, it looks thinner and emaciated. |
| 5 | Death | |

All mice having scores of 1 and above were considered sick.

Animals with a score of 4 for more than two days were given a score of 5 and sacrificed for humane reasons. For calculation purposes, the score (5) of animals that are sacrificed or died will be carried forward (LOCF).

Interpretation of Results

Calculation of the Incidence of Disease (Disease Ratio)

The number of sick animals in each group was summed. The incidence of disease was calculated as $$\text{INCIDENCE of DISEASE} = \left(\frac{\text{No. of sick mice in treated group}}{\text{No. of sick mice in control group}}\right)$$

The percent inhibition according to incidence was calculated as:

$$\text{INHIBITION (\%) of INCIDENCE} = \left(1 - \frac{\text{Number of sick mice in treated group}}{\text{Number of sick mice in control group}}\right) \times 100$$

Calculation of the Mortality/Moribundity Rate (Mortality Ratio)

The number of dead or moribund animals in each group was summed.

The mortality of disease was calculated as $$\text{MORTALITY of DISEASE} = \left(\frac{\text{No. of dead or moribound mice in treated group}}{\text{No. of dead or moribound mice in control group}}\right)$$

The percent inhibition according to mortality was calculated as $$\text{INHIBITION (\%) of MORTALITY} = \left(1 - \frac{\text{Number of dead or moribound mice in treated group}}{\text{Number of dead or moribound mice in control group}}\right) \times 100$$

Calculation of Duration of Disease

The mean duration of disease expressed in days was calculated as $$\text{Mean Duration} = \left(\frac{\sum \text{Duration of disease of each mouse}}{\text{No. of mice in the group}}\right)$$

Calculation of Mean Delay in Onset of Disease

The mean onset of disease expressed in days was calculated as $$\text{Mean Onset} = \left(\frac{\sum \text{Onset of disease of each mouse}}{\text{No. of mice in the group}}\right)$$

The onset of disease for a mouse that did not develop EAE is considered as 24 days (One day after termination of study). The mean delay in onset of disease expressed in days is calculated by subtracting the mean onset of disease in control group from test group.

Calculation of the Mean Maximal Score and Percent Inhibition

The mean maximal score (MMS) of each group was calculated as $$MMS = \left(\frac{\sum \text{Maximal Score of each mouse}}{\text{No. of mice in the group}}\right)$$

The percent inhibition according to MMS was calculated as $$\text{INHIBITION (\%) of } MMS = \left(1 - \frac{MMS \text{ of treated group}}{MMS \text{ of control group}}\right) \times 100$$

Calculation of the Group Mean Score and Percent Inhibition

The daily scores of each mouse in the test group was summed and the individual mean daily score (IMS) was calculated as $$IMS = \left(\frac{\sum \text{Daily score of mouse}}{\text{Observation period (days)}}\right)$$

The mean group score (GMS) was calculated as $$GMS = \left(\frac{\sum IMS \text{ of each mouse}}{\text{No. of mice in the group}}\right)$$

The percent inhibition was calculated as $$\text{INHIBITION (\%) of } GMS = \left(1 - \frac{GMS \text{ of treated group}}{GMS \text{ of control group}}\right) \times 100$$

Figure 1:
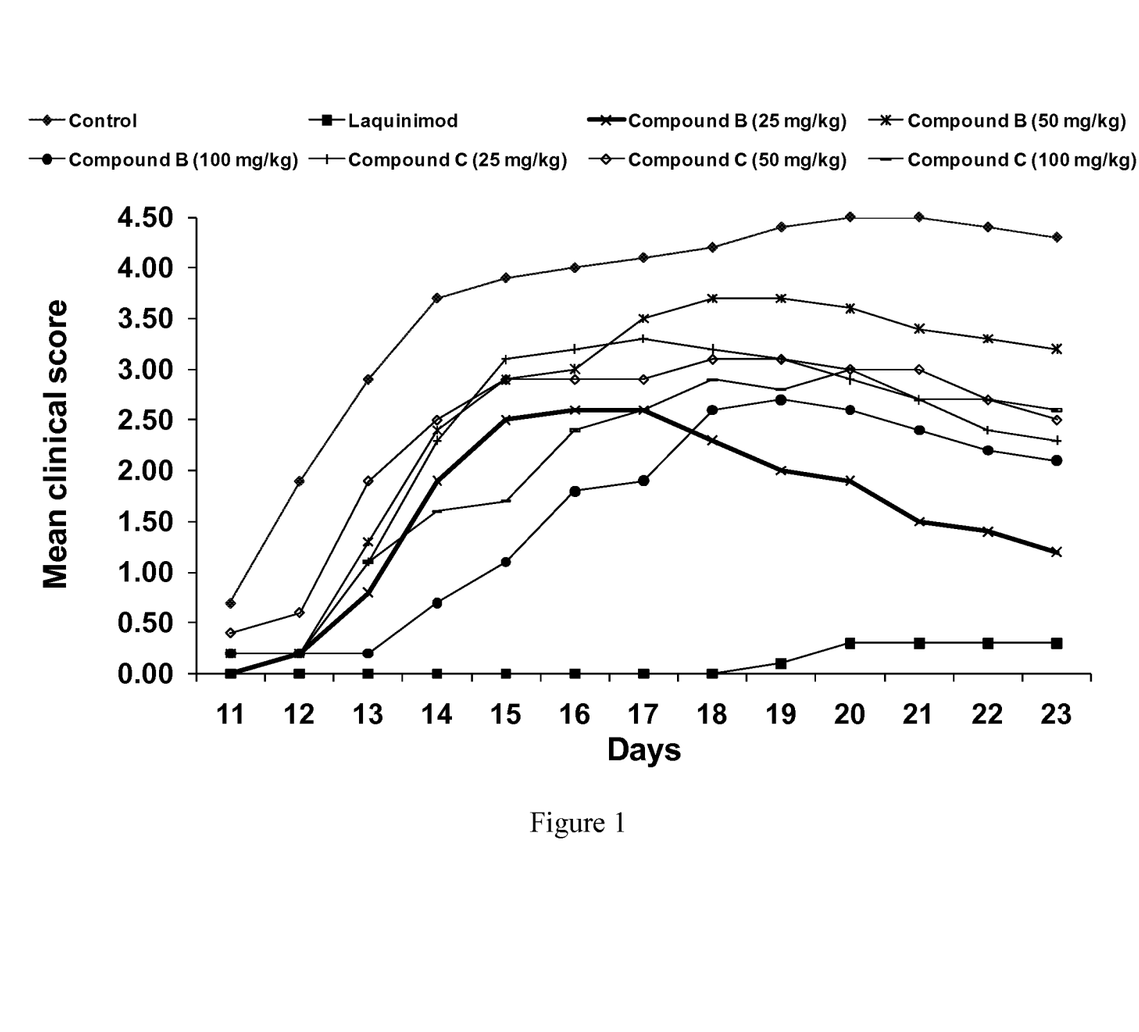
FIG. 1: Mean clinical score (GMS) based on the CSJL EAE model in mice upon treatment using compounds B and C at various doses, laquinimod (positive control) and negative control.

Results:

The 5% dextrose treated negative control group exhibited severe EAE clinical signs with 100% incidence and 80% mortality. The 1 mg/kg laquinimod treated positive control group exhibited 80% activity according to incidence, 93.5% activity according to MMS and 96.7% activity according to GMS. Compounds B and C working concentrations prepared in 5% Dextrose exhibited some activity at all dose levels. 30 to 60% mortality was observed in all groups treated with Compounds B and C except for the group treated with 25 mg/kg Compound B where no mortality was observed. Among these groups, the groups exhibiting maximal EAE inhibition were groups treated with Compound B at dose levels of 25 mg/kg (55.9% activity) and 100 mg/kg (56.4% activity) based on GMS.

Example 4

This example was performed in the same manner as example 3 with the following groups:

| Treatment Groups | dose/day |
| --- | --- |
| 0.5% methyl cellulose (negative control) | 10 ml/kg daily (BD) from Day 0 to 22 |
| laquinimod (positive control) | 1 mg/kg daily (QD) from Day 0 to 22 |
| Compound B | 15 mg/kg (BID) from Day 0 to 22 |
| | 25 mg/kg (BID) from Day 0 to 22 |
| Compound A | 25 mg/kg (BID) from Day 0 to 22 |
| | 50 mg/kg (BID) from Day 0 to 22 |
| | 100 mg/kg (BID) from Day 0 to 22 |

Treatments in all groups were administered orally.

Compound A was prepared for administration by mixing in 0.5% methyl cellulose (0.5% MC) to concentrations of 2.5, 5.0 and 10 mg/ml for dose levels of 25, 50 and 100 mg/kg respectively. The samples were vortexed and sonicated until a clear solution was obtained.

Test samples were freshly prepared.

The 2.5, 5.0 and 10 mg/ml concentrations of Compound A were administered orally, twice daily (BID) from initiation of study until study termination (Day 23) at a volume dose of 0.2 ml/mouse.

Compound B was prepared for administration as in Example 3.

The vehicle (0.5% MC) was administered to the negative control group orally, twice daily (BID) from the initiation of the study until study termination (Day 23).

Figure 2:
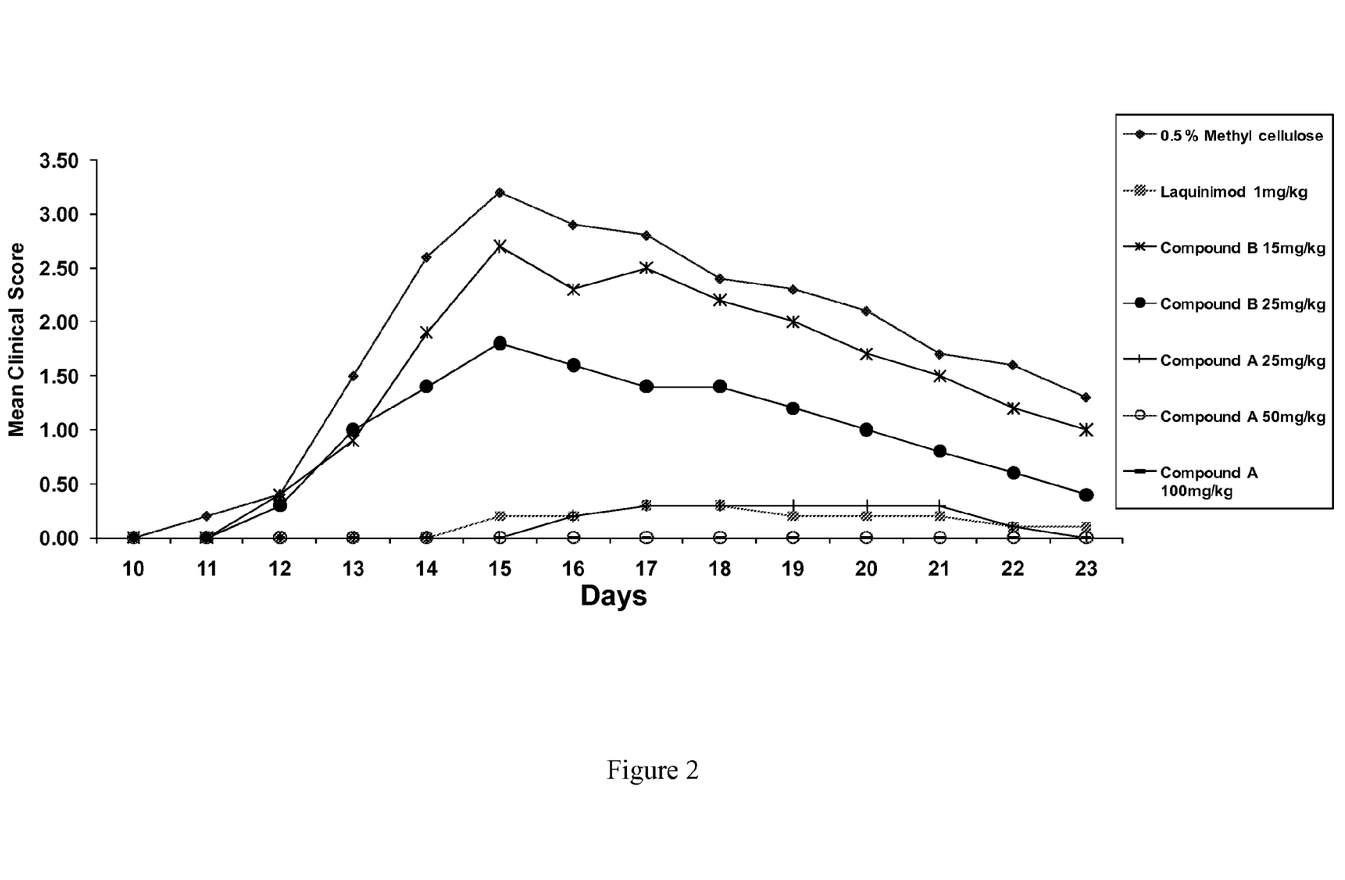
FIG. 2: Mean clinical score (GMS) based on the CSJL EAE model in mice upon treatment using compounds A and B at various doses, laquinimod (positive control) and negative control.

Results:

The data show that the efficacy of Compound A was better than Compound B. Treatment with 15 and 25 mg/kg of Compound B showed moderate activity. In contrast, treatment with Compound A at 25, 50 and 100 mg/kg showed almost complete protection from disease onset and severity at all doses tested.

DISCUSSION

Riluzole (6-trifluoromethoxy-2-amino-benzothiazole) is a pharmacological agent potentially useful to slow down the evolution of amyotrophic lateral sclerosis, a neurologic disorder. (Ben Simon et al., New Engl. J. Med., 330:585-91 (1994)). PCT International Publication No. WO 01/95907 suggests the use of Riluzole for treatment or prevention of the onset of symptoms of multiple sclerosis. PCT International Publication No. WO 00/74676 suggests the use of Riluzole for treatment of multiple sclerosis either alone or in combination with other drugs.

6-trifluoromethoxy-2-amino-benzothiazole, PK 26124, RP 54274, Riluzole, was synthesized for the first time by a Russian group (J. Gen. Chem. USSR, 1963, 33, 2240-2246; U.S. Pat. No. 2,822,359; Ch. A., 52, 8570d, 1958) as a part of their investigation on the influence of electronegative substituents at the 6 position of the benzothiazole nucleus on the color of diazastyryl bases.

2-Aminobenzothiazoles exist in tautomeric forms (where the proton is shifted between the 2-amino group and the ring nitrogen). When this process is blocked by complete alkylation of the 2-amino group or by alkylation of the ring nitrogen to give for instance 2-imino-3-methylbenzothiazoline, the depressant effect of the 2-aminobenzothiazole is changed to stimulation of the CNS (Domino, E. F. et al., J. Pharmacol. Exp. Ther., (1952) 105: 486-497). Domino and co-workers have also shown that the azole structure is essential for the paralyzing effect of the benzazoles, since opening that ring system resulted in convulsing activity. None of the benzazoles had any curare-like action in doses producing paralysis.

A group of 6-trifluoromethoxy-2-amino-benzothiazoles bearing a variety of substituents on the amino group was generically disclosed in European Patent No. EP 282 971 and U.S. Pat. Nos. 4,826,860, 4,918,090, and 4,971,983, as effective for treating cerebrovascular disorders.

U.S. Pat. No. 4,535,088 discloses propynylaminothiazole derivatives having anti-fungal and/or anti-microbial activity.

U.S. Patent Application 2004/0176430 describes propargyl-trifluoromethoxy-amino-benzothiazole derivatives in which the amino-propargyl moiety is directly bound to the benzothiazole ring.

The results with Compounds A, B and C herein further show the effects of aminobenzothiazole modification.

What is claimed is:

1. A compound according to the formula:

wherein $R_1$ is —$CH_2NR_2$— or an N-containing heterocycloalkyl, wherein $R_2$ is H or C1-C4 alkyl, or a pharmaceutically acceptable salt thereof.

2. The compound or a pharmaceutically acceptable salt of the compound according to claim 1, wherein R, is N-containing heterocyclohexane.

3. The compound or a pharmaceutically acceptable salt thereof according to claim 2, wherein the N-containing heterocyclohexane is piperazine or piperidine.

4. The compound or a pharmaceutically acceptable salt of the compound according to claim 3, wherein $R_1$ is piperazin.

5. The compound according to claim 4 of the formula:

or a pharmaceutically acceptable salt thereof.

6. The compound or a pharmaceutically acceptable salt of the compound according to claim 1, wherein $R_1$ is —$CH_2NR_2$—, and $R_2$ is selected from the group consisting of H and $CH_3$.

7. The compound according to claim 6 of the formula:

or a pharmaceutically acceptable salt thereof.

8. The compound according to claim 6 of the formula:

or a pharmaceutically acceptable salt thereof.

9. The pharmaceutically acceptable salt of a compound according to claim 1 which is a hydrochloride salt.

10. The pharmaceutically acceptable salt of a compound according to claim 1 which is a mesylate salt.

11. A pharmaceutical composition comprising the compound of a pharmaceutically acceptable salt of claim 1 and a pharmaceutically acceptable carrier.

12. A process of preparing a compound having the structure:

comprising the steps of:
a) reacting under suitable conditions with an halide acid in the presence of a first solvent;
b) adding piperazine to the reaction mixture of step a) to provide c) reacting the product from step b) with propargylhalide in the presence of a second solvent; and
d) obtaining the compound from the reaction mixture of step c).

13. The process of claim 11, wherein the first solvent is a mixture of toluene and acetic acid, and the second solvent is toluene.

14. A process of manufacturing a compound having the structure:

wherein R is H or C1-C4 alkyl,
comprising the steps of:
a) reacting under suitable conditions with Lawesson's Reagent in the presence of a first solvent to provide b) reacting the product from step a) with an oxidizing agent in the presence of a second solvent to provide c) reacting the product from step b) with N-bromosuccinimide in the presence of a third solvent to provide and
d) reacting the product from step c) with in the presence of a fourth solvent; and e) obtaining the compound from the reaction mixture of step d).

15. The process of claim 14, wherein the first solvent is THF, the second solvent is ethanol, the third solvent is $CCl_4$, and the fourth solvent is acetonitrile.

16. A method for treating a subject afflicted with an autoimmune disorder comprising administering to the subject a therapeutically effective amount of the compound or pharmaceutically acceptable salt thereof of claim 1 so as to thereby treat the subject's autoimmune disorder, wherein the autoimmune disorder is multiple sclerosis.

17. The method of claim 16, wherein the therapeutically effective amount is administered daily.

\* \* \* \* \*